United States Patent [19]

Tamburini et al.

[11] Patent Number: 5,833,946
[45] Date of Patent: Nov. 10, 1998

[54] DISSEMINATION OF FUNGAL INFECTIONS: ANIMAL MODEL AND METHOD OF PROPHYLAXIS

[75] Inventors: Paul Perry Tamburini, Kensington; Edward David Huguenel, Guilford; Kimberly Ann Fallon, Bethany, all of Conn.

[73] Assignee: Bayer Corporation, West Haven, Conn.

[21] Appl. No.: 465,039

[22] Filed: Jun. 6, 1995

[51] Int. Cl.$^6$ .......................... G01N 31/00; G01N 33/48; A61K 49/00
[52] U.S. Cl. ...................... 424/9.2; 424/274.1; 424/184.1
[58] Field of Search ................................ 424/450, 184.1, 424/9.2, 274.1; 514/32, 37, 42, 54

[56] References Cited

U.S. PATENT DOCUMENTS

| | | | |
|---|---|---|---|
| 3,740,319 | 6/1973 | Umezawa et al. | 195/80 R |
| 3,784,686 | 1/1974 | Miller et al. | 424/94 |
| 3,840,516 | 10/1974 | Umezawa et al. | 260/112.5 |
| 3,869,347 | 3/1975 | Umezawa et al. | 195/80 R |
| 3,873,681 | 3/1975 | Miller | 424/9 |
| 3,906,085 | 9/1975 | Miller | 424/9 |
| 3,975,366 | 8/1976 | Umezawa et al. | 260/112.5 R |
| 4,091,093 | 5/1978 | Kojima et al. | 424/177 |
| 4,185,096 | 1/1980 | Castro et al. | 424/177 |
| 4,206,283 | 6/1980 | Kojima et al. | 435/70 |
| 4,339,439 | 7/1982 | Buyniski et al. | 424/177 |
| 4,348,386 | 9/1982 | Kojima et al. | 424/177 |
| 4,663,167 | 5/1987 | Lopez-Berestein et al. | 514/37 |
| 4,725,580 | 2/1988 | Wagnon et al. | 514/17 |
| 4,737,488 | 4/1988 | Lockhoff et al. | 514/42 |
| 4,746,648 | 5/1988 | Wagnon et al. | 514/17 |
| 4,761,402 | 8/1988 | Williams | 514/54 |
| 4,840,935 | 6/1989 | Wagnon et al. | 514/18 |
| 4,900,722 | 2/1990 | Williams | 514/54 |
| 4,978,654 | 12/1990 | Lopez-Berestein et al. | 424/450 |
| 5,120,718 | 6/1992 | Goldman et al. | 514/32 |

FOREIGN PATENT DOCUMENTS

| | | | |
|---|---|---|---|
| 9115121 | 10/1991 | WIPO | A01N 37/18 |
| 5178807 | 7/1993 | WIPO . | |
| 5178825 | 7/1993 | WIPO . | |
| 5178827 | 7/1993 | WIPO . | |
| 9424150 | 10/1994 | WIPO | C07K 5/02 |

OTHER PUBLICATIONS

Morrison et al, Infect. & Immun. , May 1993, pp. 2030–2036.
Fusek et al, Adv Exp Medicine & Bio, 1995, pp. 489–500, v362.
de Repentigny et al, Infect & Immun., Nov. 1992, pp. 4907–4914.
Tumminello et al, Med Res Reviews, v 13, No. 2, pp. 199–208, 1993.
Karyotakis et al, JInfectious Diseases, 1993, 168:1311–3.
Borg et al, Infect. and Immun., Mar. 1988, pp. 626–631.
Cole et al, J Med Vet Myrol, 1989, 27(6) pp. 363–380.
Zotter et al, Dermatol Monatsschr, 1990, 176(2–3) pp. 189–198 (abst.).
Cutler, Putative Virulence Factors of Candida Albicans, Annu. Rev. Microbiol. 45, 187–218 (1991).
Togni et al., Acid Proteinase Secreted by Candida Tropicalis: Virulence in Mice of a Proteinase Negative Mutant, J. Med. Vet. Mycol., 32, 257–265 (1994).
van Etten, et al. Efficacies of amphotericin B–desoxycholate (Fungizone), liposomal amphotericin B (AmBisome) and fluconazole in the treatment of sytemic candidosis in immunocompetent and leucopenic mice, J. Antimicrob. Chemotherapy, 32, 732–739 (1993).
Tsuobi, et al., A Specific Inhibitor of Keratinolytic Proteinase from Candida albicans Could Inhibit the Cell Growth of C. Albicans, J. Invest. Dermatol., 85, 438–440 (1985).
Zotter, et al., The effect of pepstatin A on Candida albicans infection in mice, Dermatol. Mon.schr., 176, 189–198 (1990).
Rüchel, et al., Modulation of Experimental Systemic Murine Candidosis by Intravenous Pepstatin, Zbl. Bakt., 273, 391–403 (1990).
Ross, et al., The secreted aspartate proteinase of Candida albicans: physiology of secretion and virulence of a proteinase–dificient mutant, J. Gen. Microbiology, 136, 687–694 (1990).
Field, et al., Persistence and Spread of Candida albicans After Intragastric Inoculation of Infant Mice, Infection and Immunity, 31, 783–791 (1981).
Ghannoum, et al., Correlative relationship between proteinase production, adherence and pathogenicity of various strains of Candida albicans, J. Med. and Vet. Mycology, 24, 407–413 (1986).
Toshitsugu Nakamura, Experimental pulmonary candidiasis in modified rabbits, Mycopathologia, 85, 129–144 (1984).

(List continued on next page.)

*Primary Examiner*—James C. Housel
*Assistant Examiner*—Ginny Allen Portner
*Attorney, Agent, or Firm*—William F. Gray

[57] ABSTRACT

Aspartyl protease inhibitors such as pepstatin A have been found to prevent dissemination of Candida species across an epithelial barrier in mammals. Accordingly, a method for reducing adverse biological effects of dissemination of Candida species in an immunosuppressed mammal comprises administering prophylactically to the mammal an effective amount of an inhibitor of an aspartyl protease. Also, a method for identifying medicaments useful for preventing or treating systemic Candidiasis comprises treating test and control groups of immunosuppressed mammals with vehicle comprising a potential medicament, and with vehicle alone, respectively; administering to the test and control groups of mammals at least one Candida species, via the airways, at a time subsequent to the treating step if prophylactic medicaments are to be evaluated, but at a time prior to initiation of the treating step if therapeutic medicaments are to be evaluated; monitoring for a biological response of the test and control groups of mammals to the treating and administering steps; and comparing the biological response of the test and control groups of mammals over time.

5 Claims, 3 Drawing Sheets

OTHER PUBLICATIONS

Balish, et al., Colonization of Congenitally Athymic, Gnotobiotic Mice by Candida albicans, Applied and Environmental Microbiology, 47, 647–652 (1984).

Ekenna, et al., Factors Affecting Colonization and Dissemination of Candida albicans from the Gastrointestinal Tract of Mice, Infection and Immunity, 55, 1558–1563 (1987).

Pope, et al., Sytemic and Gastrointestinal Candidiasis of Infant Mice After Intragastric Challenge, Infection and Immunity, 25, 702–707 (1979).

Ray, et al., Comparative Production and Rapid Purification of Candida Acid Proteinase from Protein–Supplemented Cultures, Infection and Immunity, 58, 508–514 (1990).

Kwon–Chung, et al., Genetic Evidence for Role of Extracellular Proteinase in Virulence of Candida albicans, Infection and Immunity, 49, 571–575 (1985).

Kobayashi, et al., A Role of Secreted Proteinase of Candida albicans for the Invasion of Chick Chorio–Allantoic Membrane, Microbiol. Immunol., 33, 709–719 ( 1989).

El–Magharabi, et al., Characterization of Candida albicans epidermolytic proteases and their role in yeast–cell adherence to keratinocytes, Clinical and Experimental Dermatology, 15, 183–191 (1990).

Chakrabarti, et al.,In vitro proteinase production by Candida species, Mycopathologia, 114, 163–168 (1991).

De Bernardis, et al., Evidence for a Role for Secreted Aspartate Proteinase of Candida albicans in Vulvovaginal Candidiasis, J. of Infectious Diseases, 161, 1276–1283 (1990).

Cassone, et al., Evidence for a Correlation Between Proteinase Secretion and Vulvovaginal Candidosis, J. of Infectious Diseases, 156, 777–783 (1987).

Rüchel, et al., Candida acid proteinases, J. of Medical and Veterinary Mycology, 30, 123–132 (1992).

Segal, E., Chapters 5 & 6, pp. 49–76, CRC Press, 1994.

Sandovsky–Losica et al., Immun. Infect. Dis., vol. 3, pp. 155–159, 1993.

Goldman, R.C. et al., Infectious Agents and Disease, vol. 4, pp. 228–247, 1995.

Fusek, M. et al., Biochem., 1994, vol. 33, pp. 9791–9799.

Ruchel, R. et al., 261. Bakt, vol. 273, pp. 391–403, 1990.

FIG. 3

DISSEMINATION OF FUNGAL INFECTIONS: ANIMAL MODEL AND METHOD OF PROPHYLAXIS

FIELD OF THE INVENTION

This invention relates to fungal infections, and more particularly, to a method for reducing mortality associated with dissemination of such infections, and to an animal model for identifying potential medicaments against such infections.

BACKGROUND

Candidiasis incidence, diagnosis, and treatment

*Candida sp.* are opportunistic fungal pathogens that are present on epithelial surfaces and within the GI tract of mammals. Disseminated (systemic) candidiasis, a disease that is steadily increasing in incidence, is most prevalent in immunosuppressed, (particularly neutropenic) patients, and is usually established following passage of the organism across the mucosal epithelium and into the blood stream (Odds F. C., Candida and Candidosis, 2nd Ed., Bailliere Tindall, London(1988)). It is notoriously difficult to diagnose. Amphotericin B is the most effective available therapy for disseminated candidiasis, but its toxicity has complicated its use (van Etten et al., J. Antimicrob. Thera., 32, 723 (1993)).

Animal models for study of Candidiasis

In the most frequently used animal models for treatment of candidiasis with potential medicaments, *Candida sp.* are administered intravenously (i.v.) either to normal or immuno-compromised mice, rats, or guinea pigs, the animals are treated, and both mortality and dissemination to deep organs are followed as functions of time.

Only a few models for disseminated candida infections have been described which involve passage of pathogen across an epithelial barrier, and these have not been particularly informative. Oral treatment of congenitally athymic mice with *C. albicans* via the drinking water failed to produce significant systemic mycosis (Balish et al., Appl. and Environ. Microbiol., 47, 647 (1984)). Similar observations were made with Swiss mice (Ekenna and Sherertz., Infect and Immun., 55, 1558 (1987)). Systemic candidiasis has been elicited in fasted infant mice by intragastric challenge (Pope et al., Infect and Immun., 25, 702 (1979); Field et al., Infect and Immun., 31, 783 (1981)), but usually, less than 50% of the challenged mice died, and the inherent variabilities required use of large numbers of animals to generate statistically reliable data.

Pulmonary challenge with *Candida sp.* has not been exploited for the establishment of disseminated infections. Reasons for this may be that the airways are a relatively minor route of entry for the establishment of clinical infections, or that administration of precise doses of yeasts to the lower airways is expected to be difficult. Localized pulmonary lesions have been established by airway administration of *C. albicans* to cyclophosphamide-treated rabbits (Nakamura., Mycopathologia., 85, 129 (1984)), but the potential for modeling systemic mycoses was not addressed.

Virulence factors for Candidiasis

Candida acid proteases (CAPs) are a family of 45 kD aspartyl proteases that are secreted by *Candida sp.* and are inhibited in vitro by pepstatin A (Ray and Payne., Infect and Immun., 58, 508 (1990), Tsuobi et al., J. Invest Dermatol., 85, 438 (1985)). Circumstantial evidence indicates that these proteases are virulence factors. For example, protease production by various *C. albicans* strains correlates with: 1) relative lethality in mice and capacity for deep organ colonization (Ross et al., J. Gen. Microbiol., 136, 687 (1990); Cassone et al., *J. Infect.* Disease., 156, 777 (1987); De Bernardis at al., J. Infect. Dis., 1276 (1990); Chakrabarti et al., Mycopathologia., 114, 163 (1991)); 2) adherence to epithelial cells (Ghannoum at al, J. Med. and Vet Mycol., 24, 407 (1986); El-Maghrabi et al., Clin. and Experimental Dermatol., 15, 183 (1990)); 3) the capacity for penetration of chick chorio-allantoic membranes (Kobayashi et al., Microbiol. Immunol., 33, 709 (1989). Furthermore, *C. albicans* mutants that lose their capacity to produce CAPs also lose their virulence (Ross et al., J. Gen. Microbiol., 136, 687 (1990); Kwon-Chung et al., Infect. and Immun., 49, 571 (1985).

By contrast, in vivo studies designed to directly assess the role of CAPs in supporting disseminated candidiasis showed both that the CAPs are relatively unimportant and that CAP inhibitors such as pepstatin A are without efficacy. For example, neither pepstatin A (Ruchel et al., Zbl. Bakt., 273, 391 (1990); Zotter et al., Dermatol. Mon. schr., 176, 189 (1990)) nor A-70450, a potent specific inhibitor of CAPs (Goldman et al., Congress of the International Society of Human and Animal Mycology, Adelaide, Australia (1994)), reduced mortality in a statistically significant fashion when administered prior to i.v. challenge with *C. albicans.* Furthermore, ablation of a *C. tropicalis* CAP gene had little or no effect on the virulence of the organism when administered i.v. to mice (Togni et al., J. Med. and Vet. Mycol., 32, 257 (1994)).

There is a need for effective anti-Candida agents having fewer toxicological problems than amphotericin B, and which by virtue of their lower toxicities can be administered to high risk patients either prophylactically or at the earliest sign of infection, without the need for a firm diagnosis. Also needed is an in vivo test procedure which can be used to evaluate potential medicaments for efficacy against Candida infections. These needs are met by the present invention.

SUMMARY

The present application discloses an in vivo pulmonary model of Candida infection which involves dissemination of pathogen across the airway epithelium. This provides a method for identifying medicaments which are useful for preventing or treating systemic Candidiasis, and which comprises the following steps:

treating test and control groups of immunosuppressed mammals with vehicle comprising a potential medicament, and with vehicle alone, respectively;

administering to said test and control groups of mammals at least one Candida species, via the airways, at a time subsequent to said treating step if prophylactic medicaments are to be evaluated, but at a time prior to initiation of said treating step if therapeutic medicaments are to be evaluated;

monitoring for a biological response of said test and control groups of mammals to said treating and administering steps; and comparing said biological response of said test and control groups of mammals over time.

This method for identifying medicaments involves determining the prophylactic or therapeutic effect of potential medicaments toward mammals which are challenged with *Candida sp.* via the airways. Since dissemination involves passage of the pathogen across an epithelial barrier, activities of compounds that block epithelial penetration or other steps are evaluated.

The primary advantage of the test method of the present invention over prior art methods for identifying potential medicaments useful against dissemination of Candida sp. infections is that it is able to identify medicaments which prior art test methods fail to identify because they bypass the early steps in the dissemination process. This is demonstrated by the fact that pepstatin A, which is an inhibitor of the C. albicans aspartic proteases and which showed no activity against Candida dissemination in prior art testing methods, has been shown by the method of the present invention to protect against C. albicans at potencies similar to those observed with the known antifungal agent amphotericin B.

The present invention also provides a method for reducing adverse biological effects of dissemination of Candida species in an immunosuppressed mammal, which comprises the step of administering prophylactically to the mammal an effective amount of an inhibitor of an aspartyl protease.

DESCRIPTION OF THE DRAWING

The invention will be better understood from a consideration of the following detailed description, taken in conjunction with the drawing, in which.

DETAILED DESCRIPTION

Glossary of terms, procedures, etc.

As employed herein, the below-listed abbreviations have the indicated meanings. BSA: bovine serum albumin; CAP: candida aspartyl protease; c.f.u.: colony forming units; Dns: 5-(dimethyl-amino)-naphthalene-1-sulfonyl; DMSO: dimethyl sulfoxide; HPLC: high performance liquid chromatography; I.C.50: inhibitor concentration yielding 50% inhibition; i.v.: intra-venous; KLH: Keyhole Limpet Hemocyanin; PBS: phosphate buffered saline; SDS-PAGE: sodium dodecyl sulphate polyacrylamide gel electrophoresis; WFI: water for injection; YCB: yeast carbon base; YD: yeast extract containing dextrose.

Methods and instrumentation for peptide synthesis were as discussed in Tamburini et al., Anal. Biochem., 186, 363 (1990). Amino acid analyses were performed in accordance with the teachings of Heald et al., Biochemistry, 30, 10467 (1991). Protein content of crude extracts was determined by the assay disclosed by Bradford M., Anal Biochem., 72, 248 (1976). Relevant portions of each of these references are hereby incorporated by reference.

General materials and methods for the following examples are listed below. Pepstatin A, glucose, and bovine serum albumin were obtained from Sigma (St. Louis, Mo.), Mono-Q™ columns and BrCN-activated sepharose 4B were obtained from Pharmacia (Alameda, Calif.). Bovine azo-albumin was obtained from ICN Biomedicals (Aurora, Ohio). Yeast carbon base and yeast extract were obtained from Difco (Detroit, Mich.). Sabouraud dextrose agar was obtained from Baxter Scientific (McGaw Park, Ill.). Amphotericin B was obtained from Lyophomed (Deerfield. Ill.). Cyclophosphamide was purchased as Cytoxan™ from Henry Schein Medical Supply (Woodbury, N.Y.). Ciprofloxacin was obtained from Bayer Corporation (West Haven, Conn.). Candida albicans strain ATCC 32354 was obtained from the American Type Tissue Culture Collection (Rockville, Md.).

In the method of the present invention which involves reducing adverse biological effects associated with dissemination of Candida species in an immunosuppressed mammal by administration of an aspartyl protease inhibitor, immunosuppression of the mammal may have resulted from a disease such as cancer, from myeloperoxidase deficiency, from the presence of an infectious organism such as HIV or SIV, or from any of a variety of medical treatments such as radiation therapy, chemotherapy, or intentional immunosuppression for the purpose of carrying out organ or tissue transplantation. The inhibitor is administered prophylactically or therapeutically.

The phrase "adverse biological effects" includes mortality, or morbidity, loss of organ, limb, tissue or cellular function, impaired sensory perception, loss of mobility, loss of cognition, excessive bleeding, sepsis, septic shock, fever, wasting, pain, and secondary infection due to immunosuppression.

As used herein, the term prophylactically means that the inhibitor is administered to individuals at risk of developing systemic candidiasis, regardless of whether the infectious agent has entered the blood stream of the immunosuppressed individual or not. If the infectious agent has in fact entered the blood stream, but the individual has not yet developed symptoms of candidiasis, the fact of the initial dissemination of the organism will generally not be known. It is important not to delay administration of the inhibitor until symptoms of candidiasis develop, but rather, it is preferable to begin administration of the inhibitor to immunosuppressed individuals considered to be at risk for development of candidiasis, before symptoms of the disease manifest themselves. Individuals at risk are generally regarded as those presenting a state of impaired cellular immune responses. For example, bone marrow transplantation patients with prolonged neutropenia (neutrophils<0.5×10$^9$/L for more than 20 days) have a 40% risk of developing an invasive fungal infection (Powles and Millikin., J. Antimicrobial Chemotherapy, 28, Suppl. A, 97 (1991)).

The term "therapeutically" means that the inhibitor is administered to immunosuppressed individuals who have been exposed to Candida or who exhibit signs of a microbial infection, as soon as practical, since by the time Candida can be unequivocally detected in the blood, the probability of successful treatment is low.

The medicaments of the present invention are contemplated for use in veterinary and human applications. These medicaments include all candida aspartyl protease inhibitors. They are generally compounds that contain an active center that mimics the stereochemistry of the peptide-substrate transition-state inolved in proteolysis. The medicament pepstatin A is prepared either by purification from cultured broths of *Streptomyces sp.* as described in the art (Umezawa et al., J. Antibiot., 23, 259 (1970); U.S. Pat. No. 3,740,319), or by synthesis (Morishima et al., J. Antibiot., 25, 551 (1972)). Pepstatins B (U.S. Pat. No. 3,975,366) and C are also isolated from cultured broths of *Streptomyces sp.* (Miyano et al., J. Antibiot., 25, 489 (1972)). Pepstatins D, E, F, G, H, I and J are produced from Streptomyces as described in JP 49041590 A. Other compounds besides the pepstatins that inhibit the candida protease in vitro can be used as medicaments. Examples of such compounds as well as methods for their synthesis can be found in U.S. Pat. No. 5,120,718; WO 9115121 A; JP 05178807 A; JP 05178825 A; and JP 05178827. Some of these compounds, such as those described in WO9424150 A, are pepstatin derivatives. Preparation of the candida protease inhibitor compound X and its derivatives is described in DE 4,215,874.

The medicaments are employed in pharmaceutical compositions formulated in the manner known to the art. Such compositions contain active ingredient(s) plus one or more pharmaceutically acceptable carriers, diluents, fillers, binders, and other excipients, depending on the administration mode and dosage form contemplated. Examples of therapeutically inert inorganic or organic carriers known to those skilled in the art include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like can also be added, as required to assist in the stabilization of the formulation or to assist in increasing bioavailability of the active ingredient(s) or to yield a formulation of acceptable flavor or odor in the case of oral dosing. The inhibitor employed in such compositions may be in the form of the original compound itself, or optionally, in the form of a pharmaceutically acceptable salt. The compositions so formulated are selected as needed for administration of the inhibitor by any suitable mode known to those skilled in the art.

Parenteral administration modes include intravenous (i.v.), subcutaneous (s.c.) and intramuscular (i.m.) routes. Intravenous administration can be used to obtain acute regulation of peak plasma concentrations of the drug as might be needed, for example, to treat acute fungal induced septicemia. For hospitalized neutropenic patients at extreme risk of developing candidiasis, the drug can be administered at a desired rate continuously by i.v. catheter. Improved half life and targeting of the drug to phagosomes involved in Candida killing or to epithelial surfaces may be aided by entrapment of the drug in liposomes. It should be possible to improve the selectivity of liposomal targeting by incorporating into the outside of the liposomes ligands that bind to macromolecules specific to target organs/tissues such as the GI tract and lungs. Alternatively, i.m. or s.c. depot injection with or without encapsulation of the drug into degradable microspheres (e.g. comprising poly DL-lactide-co-glycolide) or protective formulations containing collagen can be used to obtain prolonged sustained drug release. For improved convenience of the dosage form it is possible to use an i.p. implanted reservoir and septum. Improved convenience and patient compliance may also be achieved by use of either injector pens (e.g. the Novo Pin or Q-pen) or needle-free jet injectors (e.g. from Bioject, Mediject or Becton Dickinson). Precisely controlled release can also be achieved using implantable pumps with delivery to the desired site via a cannula. Examples include the subcutaneously implanted osmotic pumps available from ALZA such as the ALZET™ osmotic pump.

Nasal delivery may be achieved by incorporating the drug into bioadhesive particulate carriers (<200 $\mu$m) such as those comprising cellulose, polyacrylate or polycarbophil, in conjunction with suitable absorption enhancers such as phospholipids or acylcarnitines. Commercially available systems include those developed by Dan Biosys and Scios Nova.

Pulmonary delivery represents a nonparenteral mode of administration of the drug to the circulation. The lower airway epithelia are highly permeable to a wide range of proteins of molecular sizes up to about 20 kDa. Micron-sized dry powders containing the medicament in a suitable carrier such as mannitol, sucrose or lactose may be delivered to the distal alveolar surface using dry powder inhalers such as those of Inhale, Dura, Fisons (Spinhaler), and Glaxo (Rotahaler), or Astra (Turbohaler) propellant based metered dose inhalers. Solution formulations with or without liposomes may be delivered using ultrasonic nebulizers.

Oral delivery may be achieved by incorporating the drug into tablets, coated tablets, dragées, hard and soft gelatin capsules, solutions, emulsions, suspensions or enteric coated capsules designed to release the drug into the colon where digestive protease activity is low. Examples of the latter include the OROS-CT/Osmet™ system of Alza and the PULSINCAP™ system of the R. P. Scherer Company. Other systems use azo-crosslinked polymers that are degraded by colon-specific bacterial azoreductases, or pH sensitive polyacrylate polymers that are activated by the rise in pH in the colon. The above systems may be used in conjunction with a wide range of available absorption enhancers.

Rectal delivery may be achieved by incorporating the drug into suppositories.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of CAP which must be inhibited in order to treat the condition. As the active materials contemplated in this invention are deemed to be nontoxic, treatment preferably involves administration of an excess of the optimally required amount of active agent.

In the claimed method for reducing adverse biological effects of Candida dissemination, the inhibitor of an aspartyl protease is preferably a pepstatin, and most preferably pepstatin A. It is preferably administered parenterally by needle or i.v. catheter, or orally.

In the method for identifying medicaments useful for preventing or treating systemic Candidiasis, the mammals employed in the test procedure are preferably mice or rats, most preferably mice.

The Candida species used to challenge the test animals are selected from the group consisting of *Candida albicans, Candida tropicalis, Candida kruseii,* or *Candida parapsillosis,* and is preferably *Candida albicans.*

Immunosuppressed mammals employed in this invention are either congenitally immunocompromised or immunosuppressed by a chemical reagent. Examples of the former include C5 complement deficient mice (e.g. DBA/2N mice), congenitally athymic (nude) mice, and Scid mice.

Chemically-induced immunsuppression in mammals can be produced by any of a variety of reagents including myelo-suppressive alkylating agents such as cyclophosphamide, anti-metabolites such as 5-fluoro-uracil, plant alkaloids such as vinblastin, antibiotics such as doxorubicin, triamcinolone acetonide, cyclosporins, cytochalasin and steroids such hydrocortisone acetate, and cortisone acetate. Alternatively, immunosuppression can be induced by thymectomy and/or treatment with anti-thymocyte antiserum. Immunosuppression is preferably induced by means of a chemical agent. Such chemical agents are typically administered i.p, i.m., i.v. or s.c., depending on the pharmacologic properties of the agent. With most immunosuppressive agents, i.p. administration is preferred in practice and i.v. administration is less preferred. Administration is carried out on a regular basis, the frequency of which is sufficient to maintain the mammal in a constant state of immunosuppression over the time frame of the experiment.

Candida can be administered to mammals intranasally as a solution, intratracheally as a solution, or as an aerosol. When administered intranasally or intratracheally, the animals must be anaesthetized. The type of anesthetic is not critical but can be a barbiturate such as pentobarbital.

In some types of experiments in which dissemination of the *Candida sp.* into different organs of the animal is to be determined, it is desirable to administer an antibacterial agent such as ciprofloxacin or ceftriaxone from the time of challenge with *Candida sp.* to block opportunistic bacterial infections from interfering with the determination of organ c.f.u. Other antibacterial agents can also be used. Such antibacterials are administered regularly at a dose and frequency sufficient to suppress bacterial infections in the mammal.

To assess the efficacy of potential medicaments, the amount of Candida administered is preferably that which causes between 50 and 95% mortality over a period of 4 to 7 days. This amount is determined empirically, from the mortality produced by various amounts of administered *Candida sp.*

The test compound is administered through any of a variety of routes including i.m., s.c, i.v., i.p., p.o., or via the drinking water, depending on the pharmacology of the compound. Preferably, i.p. or i.v. administration is used for test compounds which are polypeptides. The method for treatment with the test compound is designed to maintain the plasma concentration of the material above a desired minimal plasma concentration, usually for the time frame of the experiment. Treatment can be by frequent i.p or i.v. administration of a constant dose of test compound, or by continuous infusion of test compound using s.c. depot injection or an implantable osmotic pump. In some cases, treatment involves a single dose of test compound that is administered either prior to challenge with Candida for measuring prophylactic effects, or soon after challenge with Candida for measuring therapeutic effects.

Separate groups of test animals will receive different doses of test compound (including no dose), administered in a vehicle the volume and composition of which are the same for each dose level. To measure prophylactic effects of potential medicaments, treatment with test compound is begun prior to airway challenge with *Candida sp.,* and usually continues to the end of the experiment. For measurement of therapeutic effects of test compounds against established infections, treatment with test compound is initiated from a desired time point after the airway challenge with *Candida sp.* and is usually continued to the end of the experiment. The end of the experiment is usually reached when all of the animals receiving vehicle containing a zero dose of the test compound have died, especially if no significant reduction in mortality is observed in the treated groups. In cases where there is an obvious reduction in mortality in the treated groups, such groups are monitored beyond the point at which the zero dose group has died to see if the reduction in mortality reflects permanent protection of individual animals or simply a slowing in the rate of the dissemination process such that all of the treated animals would also eventually die.

The biological response of the test animals to the treating and administering steps is measured. One form of biological response that is measured is the effect of treatment of test animals with the test compound on the survival of animals over time. Survival of animals over time is compared between the groups of animals receiving different doses of the test compound. The concentration range of test compound over which a protective effect is observed is determined.

Another biological response of the test animals that may be measured is the reduction of Candida c.f.u. in the organs of the test animals resulting from treatment with the test compound. This biological response is measured for test compounds that are found to reduce mortality. Experiments are performed as described above except that representative animals from each group are sacrificed at various times following challenge with *Candida sp.,* and their organs examined to determine organ c.f.u. by methods known to those skilled in the art. The doses of test compound that block Candida dissemination from the lungs to the liver, spleen, kidney and/or blood are used to corroborate potencies derived based on reduction in mortality.

Anti-Candida potency of potential medicaments is quantified according to reductions in mortality or organ c.f.u. resulting from known doses of the medicament, in the manner known to the art. Typically, potencies are expressed as the amount of medicament, on a mg/Kg basis, that must be administered at a defined frequency to reduce the mortality or mortality rate of the vehicle-treated group by half.

EXAMPLE 1

Detection of multiple proteases secreted by *C. albicans* ATCC 32354 grown in albumin-supported culture.

To determine if *C. albicans* ATCC 32354 is a typical protease-producing strain, protease activity was measured under conditions known to induce protease production in other commonly used pathogenic strains of *C. albicans*. *Candida albicans* (ATCC 32354) was streaked on a Sabouraud dextrose agar plate from a frozen glycerol stock and grown overnight at 37° C. A single colony was transferred to 10 ml of yeast carbon base (YCB) containing 0.2% BSA (YCB/BSA) and grown overnight at 30° C. with shaking. This overnight culture (0.1 ml) was used to inoculate 10 ml YCB/BSA cultures. Growth of the cultures at 30° C. was followed as a function of time by monitoring turbidity by measuring $A_{660nm}$. BSA depletion was separately monitored by SDS-PAGE. It was found routinely that the cultures grew logarithmically until all of the BSA substrate was consumed, typically about six days, whereupon the cultures stopped growing.

The cultures were also analyzed periodically for protease activity. Aliquots (20 µl) of fermentation broth were removed and mixed with azo-albumin substrate (2.5 mg/ml stock) and reaction buffer to achieve a final volume of 0.5 ml containing broth, 1 mg/ml azo-albumin, and 200 mM sodium citrate buffer of pH 4.4. Following incubation at 37°

C. for 20 hr, the mixtures were treated with 25 μl of trichloroacetic acid on ice and centrifuged (12,000 g×12 min). The content of dye-bound non-precipitable peptides was quantified from the $A_{320nm}$ of the supernatant after correction by subtraction of the absorbance observed in an incubation devoid of protease. With this assay it was observed that an increase in protease activity of the cultures paralleled the growth of the cultures.

Accumulation of CAP immunoreactivity in the fermentation broth was also examined using the immunoblot technique. Samples of fermentation broth in 1X sample buffer were applied (15 μl/lane) to a 15 lane, 10–20% acrylamide Tricine minigel (Novex, Encinitas, Calif.). Reducing SDS-PAGE was employed according to the manufacturer's specifications at 100 V. Gels were electroblotted onto ProBlott™ membrane (Applied Biosystems, Foster City, Calif.), and developed (40° C., overnight) with a 1:26 dilution of a rabbit polyclonal antiserum elicited to a mixture of synthetic Candida aspartic protease fragments, followed by a 1:3000 dilution of secondary goat anti-rabbit IgG antiserum coupled to alkaline phosphatase (Promega, Madison, Wis.). To prepare the polyclonal antiserum, the following peptides: Cys-Asp-Lys-Pro-Arg-Pro-Gly-Gln-Ser-Ala-Asp-Phe-amide (P1)(SEQ ID NO: 1); Cys-Gln-Ala-Glu-Leu-Lys-Leu-Asp-Gly-Gln-Gly-His-Thr-Phe-amide (P2)(SEQ ID NO: 2); Cys-Phe-Leu-Arg-Ser-Ala-Tyr-Leu-Val-Tyr-Asp-Leu-Asp-Asp-amide (P3)(SEQ ID NO: 3), which contain, respectively, amino acid segments 48–58, 238–250, and 309–321 of the sequence for a secretory C. albicans protease (Hube et al., J. Med. and Vet. Mycol., 29, 129 (1991)), were synthesized, then coupled separately to maleimide-activated Keyhole Limpet Hemocyanin using the Imject™ kit (Pierce, Rockford, Ill.). A combination of the three peptides (0.25 mg of combined KLH conjugate plus 40 μg of free P2 and P3 per animal in complete Freunds adjuvant) was used to immunize male New Zealand rabbits. Rabbits were boosted in incomplete Freunds adjuvant at three week intervals. Antiserum was prepared according to standard procedures.

With the immunoblot technique, it was found that the amount of an immunoreactive band with the same apparent molecular mass as reported for the secretory Candida aspartyl proteases (approx. 42 kDa) increased with time in the culture in a fashion that paralleled both the increase in azo-albumin hydrolyzing activity and cell growth. The above experiments show that the C. albicans strain ATCC 32354 grown in an albumin-supported culture secretes both an albumin degrading protease activity and a 42 kDa protein that is immunologically related to a CAP of known sequence. Furthermore, production of the protease activity and the 42 kDa protein correlate with cell growth and albumin substrate hydrolysis.

To provide sufficient material for protease purification, overnight culture was used to inoculate six 4 L flasks, each containing 500 ml of fresh YCB/BSA (0.1 ml overnight culture for each flask). The flasks were incubated with shaking at 30° C. for 7 to 8 days, until an $A_{660nm}$ of 7 was attained. Six 0.5 L cultures of C. albicans strain ATCC 32354 in YCB/BSA were centrifuged (5,000 g×30 min) and the supernatant (2.7 L) was passed through a 0.45 μm filter, concentrated to 45 ml on a YM-10 membrane (Amicon, Beverly, Mass.) and applied at 4° C. to a mono-Q HR 10/10 ion exchange column equilibrated with 50 mM Tris-HCl buffer, pH 7.5 (buffer A). The column was washed with 80 ml of buffer A before elution of the bound protein in a 240 ml linear gradient of 0 to 0.5M NaCl in buffer A. The $A_{280nm}$ of the eluent was monitored. The flow rate was 2 ml/min throughout. Fractions (4 ml) were collected, analyzed by SDS-PAGE/immunoblot, and assayed for proteolytic activity.

When the proteolytic activity of the chromatographic fractions was quantified according to their ability to degrade azo-albumin, three consecutively eluting peaks of protease activity defined as peaks I, II, and III, were identified when late stationary phase culture was fractionated. Pooled fractions containing the peak II and III protease activities each contained a 42 kDa protein that was greater than 95% pure by SDS-PAGE using coomassie blue staining. The peak I protease activity when pooled contained several proteins. The peak II protease was the most abundant of the three activities. Three liters of spent fermentation broth typically yielded 10 mg of pure peak II, and 2 to 3 mg of pure peak III protease. The peak II protease, but not peak I or III protease, reacted on immunoblots with the anti-peptide antibody that had been affinity purified over an immobilized peptide Cys-Phe-Leu-Arg-Ser-Ala-Tyr-Leu-Val-Tyr-Asp-Leu-Asp-Asp-amide (P3)(SEQ ID NO: 3) related to the cloned Candida aspartyl protease (Hube et al., J. Med. and Vet., Mycol., 29, 129 (1991)). The co-elution from mono-Q of the peak II and III enzymatic activity with highly pure 42 kDa proteins supports the notion that at least part of the protease activity secreted by ATCC 32354 results from the actions of a 42 kDa member of the Candida aspartyl protease family.

EXAMPLE 2

Effect of pepstatin A on the in vitro activity of proteases that are secreted by C. albicans ATCC 32354.

The proteases secreted by C. albicans ATCC 32354 also hydrolyzed the fluorescent peptide Dns-Ile-Ser-Glu-Val-Asn-Leu-Asp-Ala-Glu-Phe-Arg-amide (SEQ ID NO: 4), abbreviated Dns-ISEVNLDAEFR-amide. Aliquots of the protease-containing fractions recovered from mono-Q chromatography described in Example 1 (2 to 10 μl) were incubated with 30 μM final concentration of the fluorescent substrate Dns-ISEVNLDAEFR-amide at 37° C. in 60 μl 50 mM sodium citrate buffer of pH 4.4 for 15 minutes, after which reactions were terminated by addition of 50 μM pepstatin A in 33% v/v methanol to 10 μM final concentration, and set aside for HPLC analysis. HPLC instrumentation and general chromatographic conditions were as described Tamburini et al., Anal Biochem., 186, 363, (1990), except that $C_{18}$ separations were achieved isocratically over 8 min in 100 mM sodium acetate of pH 6.5 containing 27% (by vol.) acetonitrile, and calibrated using authentic standards. Unconverted Dns-ISEVNLDAEFR-amide (RT=5.55 min) and fluorescent products eluting at 4.2 min (Dns-Ile-Ser-Glu-Val-Asn-Leu (SEQ ID NO: 5), and 3.0 min (unidentified), were resolved and detected fluorimetrically.

Reassay of individual mono-Q column fractions from Example 1 as well as pooled fractions containing the peak I, II, or III activities showed that each of the three peaks of azo-albumin hydrolyzing activity could also hydrolyze Dns-ISEVNLDAEFR-amide at the L-D bond. The peak I and III but not peak II proteases also formed an unidentified peptide product of retention time 3.0 min.

The secretory aspartic proteases produced by other pathogenic C. albicans strains and Candida sp. are inhibitable by pepstatin A and are therefore of the aspartyl class. To determine if the peak I, II, or III protease activities secreted by ATCC 32354 were also of the aspartyl class, their susceptibility to inhibition by pepstatin A was determined. Reactions were as described above for the assay of Dns-ISEVNLDAEFR-amide cleavage by mono-Q fractions except that pepstatin A (added from a 5 mM stock in DMSO) was included in the assay mixtures at final concentrations between 0 and 100 nM, and was pre-incubated with the protease for 15 min, and reactions were terminated after 1 hr. The results are summarized in table I as I.C.$_{50}$ values.

With nanomolar potency, pepstatin A inhibited each of the peptide hydrolyzing proteases of peaks II and III, as well as one of the proteases of peak I. This shows that ATCC 32354 can secrete three chromatographically distinct aspartyl proteases. This multiplicity of aspartyl protease production observed with ATCC 32354 is consistent with the multiplicity of secreted aspartyl proteases reported for other pathogenic strains of *C. albicans* (Morrison et al., Infect and Immun., 61, 2030 (1993); Miyasaki et al., J. Bacteriol., 176 1702 (1994); Hube et al., J. Med. and Vet. Mycol., 29, 129 (1991); Wright et al., J. Bacteriol., 174, 7848 (1992) and White et al., J. Bacteriol., 175, 6126 (1993)).

TABLE I

Effect of pepstatin A on the Secretory Proteases activities of *C. albicans* ATCC 32354

| [Enzyme] | Prod (min) | V (nmol. min$^{-1}$ mg$^{-1}$) | I. C.$_{50}$ Pepstatin (nM) |
|---|---|---|---|
| I | 3.0 | 4.7 ± 0.2 | 9 |
|   | 4.2 | 2.6 ± 0.5 | N. I. |
| II | 4.2 | 497 ± 38 | 28 |
| III | 3.0 | 53 ± 8.2 | 29 |
|   | 4.2 | 31 ± 3.9 | 36 |

N. I. = no inhibition

EXAMPLE 3

Effect of aspartyl protease inhibitors on the growth of *C. albicans* ATCC 32354 in albumin-supported culture.

To study the effects of pepstatin A on growth of *C. albicans*, 0.1 ml of an overnight *C. albicans* culture was used to inoculate 10 ml cultures of either 1) YCB/BSA, or 2) a YD medium (0.2% yeast extract, 2% glucose) that contained 40 mM ammonium chloride. Pepstatin A was included in the cultures at final concentrations ranging between 0 and 10 $\mu$M (administered from a 50 $\mu$M aqueous stock). Growth of cultures at 30° C. was monitored by following A$_{660nm}$. The growth of ATCC 32354 in YCB/BSA was inhibited about 90% by 2 $\mu$M pepstatin A (table II). This effect of pepstatin was fungistatic as resuspension of arrested cells in fermentation medium devoid of pepstatin A restored cell growth. In contrast to the effects on growth in YCB/BSA, pepstatin A had no significant inhibitory effects on the growth of *C. albicans* in YD containing ammonium chloride (table II). Since ammonium chloride both removes dependence on, and suppresses the production of the secretory acid proteases, the mechanism of pepstatin inhibition action is likely to involve protease inhibition. Another aspartic protease inhibitor (compound X, Table II), that blocked with nanomolar potency (I.C.$_{50}$=110 nM) the in vitro activity of the peak II protease, also blocked growth of *C. albicans* in YCB/BSA.

This evidence shows that the aspartic proteases produced by *C. albicans* strain ATCC 32354 are necessary to support cell growth in the presence of a protein source of nitrogen. Furthermore the evidence shows that inhibition of these proteases leads to blockage of cell growth.

TABLE II

The effect of aspartyl protease inhibitors on the growth of *C. albicans* ATCC 32354 in culture.

| Medium | hours in culture | [inhibitor] | A$_{660\ nm}$ |
|---|---|---|---|
| YCB/BSA | 145 | 0 $\mu$M pepstatin A | 1.97 |
|  |  | 2.0 $\mu$M pepstatin A | 0.18 |
|  |  | 10.0 $\mu$M pepstatin A | 0.17 |
| YD + NH$_4$Cl | 145 | 0 $\mu$M pepstatin A | 2.97 |
|  |  | 2.0 $\mu$M pepstatin A | 2.99 |
|  |  | 10.0 $\mu$M pepstatin A | 3.20 |
| YCB/BSA | 168 | no compound | 3.13 |
|  |  | 10 $\mu$M compound X | 0.26 |

Compound X is 1-{92S,4S,5S)-5-[(2S)-3-(tert-Butylsulphonyl)-2-(1-naphthylmethyl) propanoyl]-(2R)-N-(tert-butoxycarbonyl)-2-amino-2-[2-(1, 3-dithiolan-2-yl)] ethanoyl] amino-6-cyclohexyl-4-hydroxy-2-(1-methyl) ethyl-hexanoyl}-s-isoleucinyl-2-pyridylamide, and is described in Example 9 of German patent DE 4,215,874.

Aliquots of cultures were removed after 48 hours, heat fixed on slides, and Gram stained (VWR Scientific, Inc., Boston, Mass.). Microscopic examination for formation of hyphae revealed that pepstatin A at concentrations of 2 $\mu$M and above inhibited the formation of hyphae in cultures grown in YCB/BSA.

EXAMPLE 4

Disseminated *C. albicans* infection produced by airway challenge with *C. albicans* ATCC 32354.

To examine the role of the protease under conditions in which the challenge dose of *C. albicans* first has to cross the airway epithelium before it can disseminate, the following procedure was developed. To both mimic the immunosuppressed patient state and increase susceptibility of the test animals to *C. albicans*, mice were rendered neutropenic by treatment with cyclophosphamide, and received concurrent ciprofloxacin treatment to block opportunistic infection by endogenous gram negative flora. In control experiments (data not shown), ciprofloxacin by itself was found to have no effect on *C. albicans* in vitro or in vivo.

Challenge inoculum was prepared by streaking *Candida albicans* (ATCC 32354) onto Sabouraud dextrose agar from a frozen glycerol stock and incubating overnight at 37° C. Five hours before challenge, the culture was re-streaked onto four Sabouraud dextrose agar slants and incubated (4 h. 37° C.). The culture was then washed from the agar slants with sterile saline, resuspended in fresh saline to achieve an A$_{660nm}$ of 0.2, and kept on ice until used. Fifty $\mu$l of a 10$^{-4}$ dilution of this challenge stock was plated to determine retrospectively the exact challenge dose in c.f.u. Female Swiss Webster mice (Charles River Breeding Laboratories, Inc., Wilmington, Mass., approx. 23 g, ten mice per group) received 125 mgKg$^{-1}$ cyclophosphamide i.p. in 0.2 ml of saline on days –5 and –3, 0, 2 and 4 of the study. On day 0, mice were anesthetized with 80 mgKg$^{-1}$ sodium pentobarbital i.p. and challenged intranasally with either 2.5×10$^5$ c.f.u. in 50 $\mu$l of saline or 50 $\mu$l of saline only (toxicity controls). On each of days 1 to 4 mice also received 50 mgKg$^{-1}$ Ciprofloxacin (i.p. in WFI/5% (w/v) glucose) to prevent bacterial infection in the immunocompromised mice. On days 0 to 4, groups of mice (n=10) received one of the following daily treatments (0.1 ml i.p.): saline, amphotericin B (0.1 to 1.0 mgKg$^{-1}$); and pepstatin A (0.06 to 6.0 mgKg$^{-1}$). Pepstatin A was dissolved in DMSO at 13.8 mgml$^{-1}$ and diluted 1:10 in saline for the 6 mgKg$^{-1}$ dose. Lower doses were diluted in normal saline serially from the 6 mgKg$^{-1}$ dose. Stock amphotericin B (5 mg/ml in WFI)

was diluted in WFI containing 5% glucose. Treatment with drug on day zero was performed three hours prior to airway challenge with *C. albicans*. Survival was monitored for fifteen days following challenge. Toxicity controls were weighed daily over the duration of treatment. Animals from parallel groups (n=10) of mice were sacrificed at various stages and used to determine organ burdens and histopathology. Organ burdens were determined in parallel in 3 mice from parallel groups that were sacrificed on days 2, 4, and 17. Mice were anesthetized with sodium pentobarbital (80 mgKg$^{-1}$), bled by cardiac puncture, and then given a lethal dose of sodium pentobarbitol. The kidneys, spleen, liver, and lungs were removed, weighed, and homogenized in 10 ml sterile PBS. Each organ homogenate (including heart blood) was serially diluted, plated on Sabauroud dextrose agar and incubated overnight at 37° C. Resulting colonies were counted to derive c.f.u./gram wet weight of organ.

For histopathology, mice from above described groups (two mice per group) were sacrificed on days 2 and 4 by administration of a lethal dose of sodium pentobarbitol. The lungs, liver, kidneys, and spleen were removed intact, embedded in paraffin, sectioned (5 μm), and stained with ammoniacal silver to visualize the Candida. Slides were stained by immersing in 4% periodic acid for 5 minutes, rinsing in distilled water five times, then immersing in a solution of ammoniacal silver (0.1% silver nitrate, 0.02% lithium hydroxide monohydrate) that had been heated by microwave (420 W for 1 min). Slides were microwaved in this solution for one minute then allowed to remain in the hot solution for one more minute before rinsing four times in distilled water and toning in 0.2% gold chloride for thirty seconds. Slides were then rinsed twice in distilled water, placed in 2% sodium thiosulfate for thirty seconds, then rinsed three times and dehydrated through graded alcohols. Finally, slides were cleared in 3–4 changes of xylene and mounted with Permount.

Figure 1A:
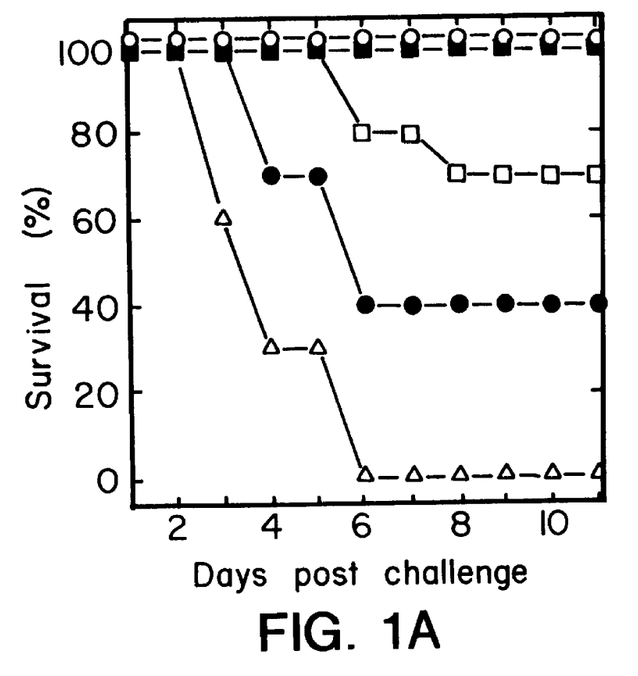
FIG. 1A shows survival times of test animals subjected to lethal airway challenge with C. albicans ATCC 32354 and treatment with amphotericin B, the treatment regimens being: saline alone (open triangles); 0.1 mgKg$^{-1}$ (closed circles); 0.5 mgKg$^{-1}$ (open squares); 1.0 mgKg$^{-1}$ (closed squares); and 1.0 mgKg$^{-1}$ but without Candida challenge (open circles).

The suitability of the model for the demonstration of antifungal effects was shown by the dose-dependent protective effect observed by pretreatment with amphotericin B. Without antifungal therapy, 100% mortality was observed within 6 days of challenge with *C. albicans* (FIG. 1A). Amphotericin B afforded complete protection at 1 mgKg$^{-1}$, and exhibited an EC$_{50}$ of approximately 0.1 mgKg$^{-1}$.

Figure 1B:
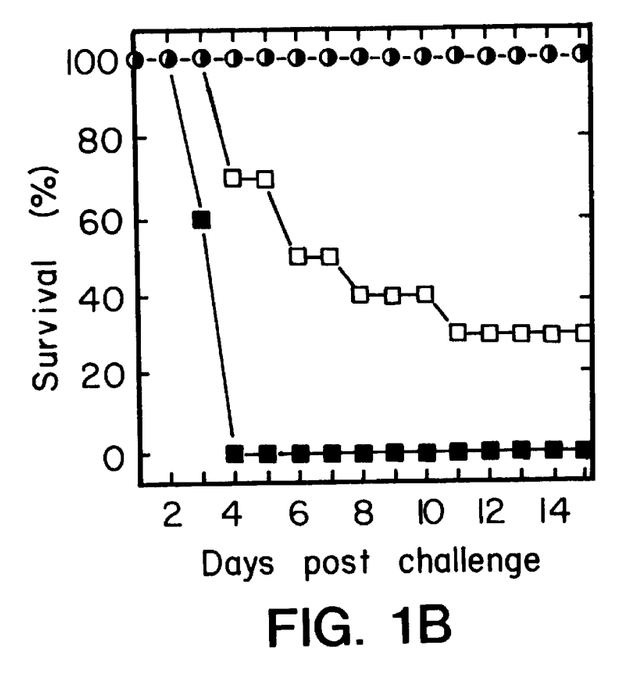
FIG. 1B shows survival times of test animals subjected to lethal airway challenge with C. albicans ATCC 32354 and treatment with pepstatin A, the treatment regimens being: saline (closed squares); 0.06 mgKg$^{-1}$ (open squares); 0.6 mgKg$^{-1}$ (closed circles); and 6 mg/Kg but without C. albicans challenge (open circles).

To explore the role of *C. albicans* aspartic proteases in experimental infection, the effect of pretreatment of mice with pepstatin A on experimentally induced candidiasis was examined. A strong protective effect was observed upon pretreating mice with pepstatin A (FIG. 1B). Protection was dose-dependent and maximal at around 0.6 mgKg$^{-1}$ where survival was 100%. In fact, pepstatin A was as potent as amphotericin B, exhibiting an EC$_{50}$ value of about 0.06 mgKg$^{-1}$.

The dramatically reduced mortality afforded by relatively low doses of pepstatin A correlated with an equally dramatic reduction in the dissemination of *C. albicans* to vital organs including the liver, kidney and spleen (Table III).

Pepstatin A completely blocked dissemination to the spleen and liver and also dramatically reduced the number of c.f.u. remaining in the lung tissue. At all doses of pepstatin A, a small number of c.f.u.'s were recovered from the kidneys. These c.f.u. may have resulted from filtration of trace c.f.u. that leaked into the blood from the lungs.

TABLE III

Effect of Pepstatin A on in vivo dissemination of *C. albicans* subsequent to intranasal challenge in immunosuppressed mice

| Pepstatin A (mg Kg$^{-1}$) | $^a$*C. albicans* (c. f. u. g$^{-1}$ homogenized tissue) × 10$^{-3}$ | | | |
|---|---|---|---|---|
| | kidney | spleen | liver | lungs |
| 0 | 39 ± 18.4 | 3.3 ± 3.1 | 5.4 ± 4.0 | 4,540 ± 2,160 |
| 0.06 | 0.67 ± 0.15 | ND | ND | 0.58 ± 0.39 |
| 0.6 | 0.49 ± 0.22 | ND | ND | 0.13 ± 0.19 |

ND = none detected.
$^a$Animals were sacrificed 4 days post challenge with *C. albicans*

Figure 2A:
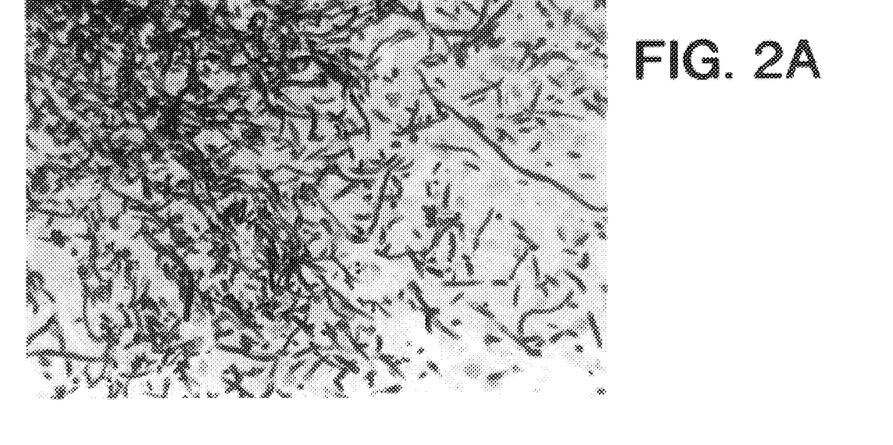
FIG. 2 presents photomicrographs of lung tissue sections from test animals subjected to lethal airway challenge with C. albicans ATCC 32354, showing C. albicans growth and hyphae formation under the following treatment regimens: (A) saline; (B) 0.06 mgKg$^{-1}$ pepstatin A; and (C) 0.6 mgKg$^{-1}$ pepstatin A.
Figure 2B:
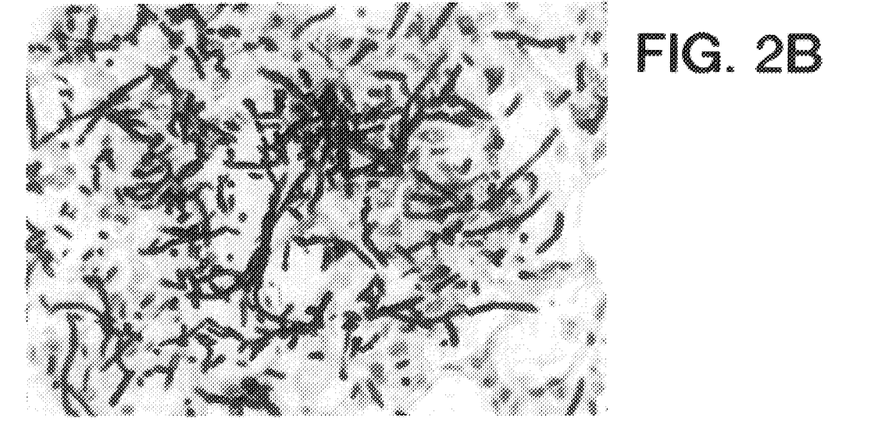
Figure 2C:
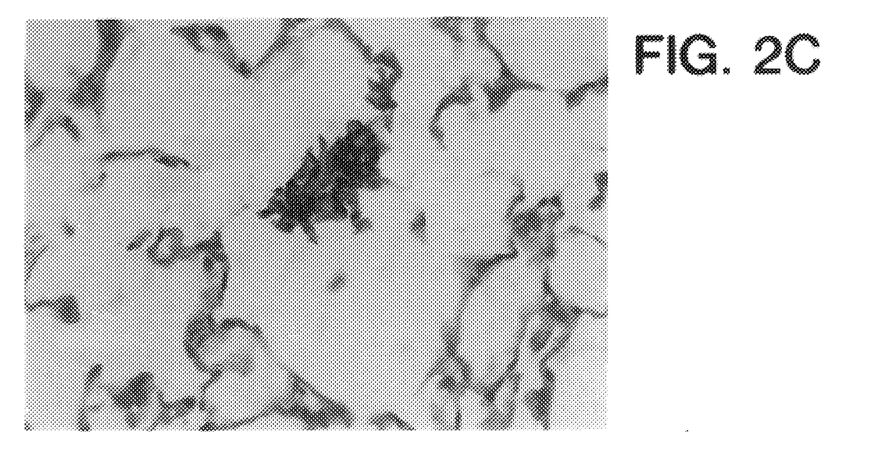

As shown in FIG. 2, histopathological analyses of lung sections fixed and stained as described above showed that administration of 0.06 and 0.6 mg/Kg$^{-1}$ of pepstatin A inhibited both the growth of *C. albicans* and hyphae formation in the lungs. This contrasted with the extensive growth and hyphae formation of *C. albicans* in the lungs of animals treated with saline. Complete protection of mice against lethal airway challenge with *C. albicans* ATCC 32354 was also observed in mice treated with 0.1 mgKg$^{-1}$ of the candida protease inhibitor compound X.

To enable a direct comparison of the airway challenge model of disseminated candidiasis with the conventional i.v. challenge model, a study of the effect of amphotericin B and pepstatin A on mortality of mice resulting from intravenous challenge with *C. albicans* ATCC 32354 was also performed.

Female Swiss Webster mice (n=10 per treatment group) were challenged by tail vein injection with 10$^6$ c.f.u. *Candida albicans* ATCC 32354 in 0.2 ml saline and mortality was monitored over the following 14 days. Three hr prior to challenge with candida, and on days 1 to 5 post challenge with candida, mice also received one of the following compounds (i.p. in saline): saline alone; 0.6 mgKg$^{-1}$ pepstatin A, or 1 mgKg$^{-1}$ amphotericin B. Challenge inoculum containing *C. albicans* was prepared in the same manner as used for airway challenge experiments except that it was adjusted to a final A$_{660nm}$ of 2.0.

Figure 3:
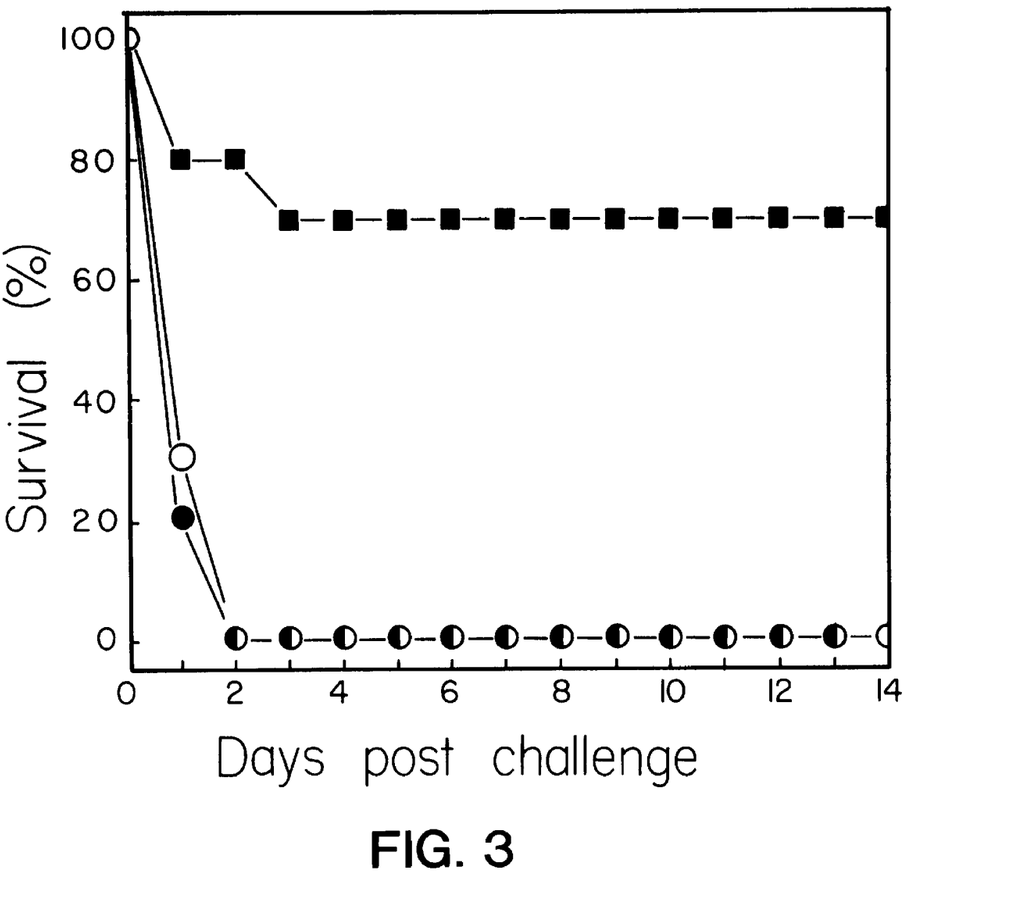
FIG. 3 is a graph showing survival times of mice challenged intravenously with a pathogenic strain of C. albicans and treated with 1 mgKg$^{-1}$ amphotericin B (closed squares), 0.6 mgKg$^{-1}$ pepstatin A (closed circles), and saline alone (open circles).

Results are presented in FIG. 3, which shows that, in contrast to the strong protective effect of pepstatin A against lethal airway challenge with *C. albicans* using the in vivo method of the present invention, pepstatin A provided no protective effect when examined using the classical i.v. challenge protocol. Mice that received saline only or pepstatin A did not survive past day two post challenge, whereas mice which received amphotericin B showed a 70% survival rate after 14 days. These data show that the method of the present invention can identify useful medicaments for Candidiasis that would be otherwise undetected using the existing classical methods. The data also explain why the prior art based on the use of classical i.v. challenge methods erroneously teaches away from the usefulness of Candida protease inhibitors as useful medicaments to treat in vivo candidiasis.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A method for identifying medicaments useful for preventing systemic Candidiasis, which comprises:

treating test and control groups of immunosuppressed mammals with vehicle comprising a potential medicament, and with vehicle alone, respectively;

administering to said test and control groups of mammals at least one Candida species, via the airways, at a time subsequent to said treating step;

monitoring for a biological response of said test and control groups of rodents to said treating and administering steps; and comparing said biological response of said test and control groups of mammals over time.

2. The method of claim 1 wherein said Candida species are selected from the group consisting of *Candida albicans, Candida tropicalis, Candida kruseii,* or *Candida parapsillosis.*

3. The method of claim 1 wherein said Candida species is *Candida albicans.*

4. The method of claim 1 wherein said mammals are mice.

5. The method of claim 1 wherein said mammals are rats.

* * * * *